Figure 1:
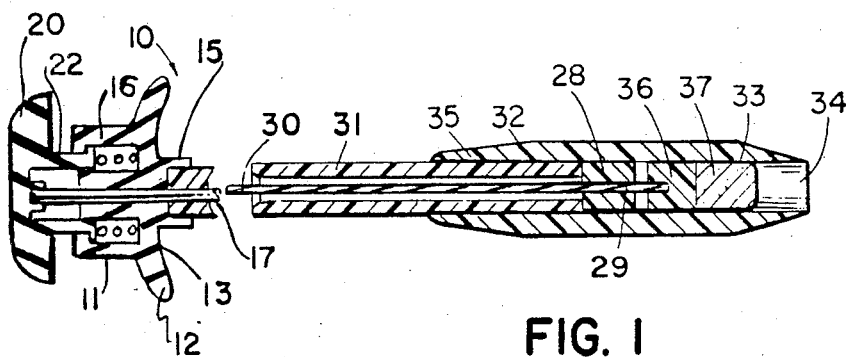

United States Patent [19]

Lemelson

[11] Patent Number: 4,588,395

[45] Date of Patent: May 13, 1986

[54] CATHETER AND METHOD

[76] Inventor: Jerome H. Lemelson, 85 Rector St., Metuchen, N.J. 08840

[21] Appl. No.: 201,531

[22] Filed: Oct. 28, 1980

Related U.S. Application Data

[63] Continuation-in-part of Ser. No. 885,263, Mar. 10, 1978, abandoned.

[51] Int. Cl.[4] .......................................... A61M 25/00
[52] U.S. Cl. ...................................... 604/59; 604/14; 604/218; 604/256; 128/1.2
[58] Field of Search .................... 128/213 R, 1.1, 1.2, 128/215-218 R, 218 P, 218 PA, 218 A, 220, 221, 235, 260, 261-262, 263-264; 604/14.15, 59.60, 218, 280, 256

[56] References Cited

U.S. PATENT DOCUMENTS

| | | | |
|---|---|---|---|
| 2,007,626 | 7/1935 | Waring | 128/264 |
| 2,170,599 | 8/1939 | Stricklin | 604/218 |
| 2,518,486 | 8/1950 | Mende | 128/261 |
| 3,043,303 | 7/1962 | Still | 128/214 E |
| 3,238,941 | 3/1966 | Klein et al. | 128/264 |
| 3,334,629 | 8/1967 | Cohn | 128/325 |
| 3,415,419 | 12/1968 | Jewett et al. | 128/218 A |
| 3,589,356 | 6/1971 | Silverman | 128/262 |
| 3,760,808 | 9/1973 | Bleuer | 128/263 |
| 3,895,634 | 7/1975 | Berger et al. | 128/263 |
| 4,023,559 | 5/1977 | Gaskell | 128/759 |
| 4,157,709 | 6/1979 | Schuster et al. | 604/14 |

FOREIGN PATENT DOCUMENTS

| | | | |
|---|---|---|---|
| 587229 | 11/1933 | Fed. Rep. of Germany | 128/263 |
| 609894 | 8/1926 | France | 128/264 |

Primary Examiner—Dalton L. Truluck

[57] ABSTRACT

A device and method are provided for disposing a quantity of matter at a select location within an animal or human body. In one form, the matter is a solid material, such as medication which dissolves with time, a source of radiation such as gamma radiation, a sensor or transducer in a housing which includes a short wave transmitter or other material or device which is operable to beneficially effect human tissue or body function when it is inserted into the body. The material is retained within a housing located at an end of a flexible tube or catheter which is inserted into a body cavity and is manipulated from the other end thereof to a predetermined location within the body cavity. Suitable actuating means located at the external end of the catheter is operated, when the head end thereof is at a predetermined location within the human body, to cause the material supported within the head to be ejected therefrom.

5 Claims, 3 Drawing Figures

CATHETER AND METHOD

Related Applications: This is a continuation-in-part of Ser. No. 885,263 filed 3/10/78 and now abandoned.

SUMMARY OF THE INVENTION

This invention relates to a medical device such as a probe, catheter or similar device which is inserted into an animal or human body through a cavity therein and manipulated so as to provide the head end of the device at a fixed location within the body. Thereafter an actuating or fluidic means disposed at the head end of the catheter is controlled in its operation from the other end of the catheter to eject or effect ejection of material from the end of the catheter which is located within the human body to cause such material to be predeterminately placed within or adjacent to a predetermined portion of internal tissue, such as an organ, growth or a damaged or abnormal portion of a body duct.

It is frequently necessary to provide a medication or other material within the human body for medicinal or investigative purposes. Such provision is frequently effected by providing an incision through the skin to the affected area requiring treatment and inserting a material in solid or fluid form through the incision to the particular area of a human body. Such procedure has a number of shortcomings including the fact that it may result in infection in the tissue which is cut, is painful, requires special treatment and dressing for recovery and repair of tissue and quite often cannot provide access to a particular organ or portion of internal tissue without major surgery and its inherent shortcomings and dangers.

Accordingly, it is a primary object of this invention to provide a new and improved apparatus and method for inserting a predetermined quantity of material into the human body.

Another object is to provide an apparatus and method for inserting a small quantity of a solid material for medicinal or repair purposes or for generating radiation adapted to serve one or more important functions such as the treatment of cancerous growths.

Another object is to provide a device including a catheter having a head portion containing a solid material which is normally maintained therein and which may be ejected therefrom under the control of an operator or physician.

Another object is to provide a catheter and head assembly therefore wherein a solid material such as a pill or other device is ejected longitudinally from the end of the catheter to dispose of adjacent internal tissue to be treated or investigated thereby.

Another object is to provide a catheter and an injection head for a solid material wherein the injection head is made of an elastomeric polymer and is so shaped by molding that an open end thereof is normally maintained closed until it is desired to eject a solid or fluid material from the end into the human body adjacent thereto.

With the above and such other objects in view as may hereafter more fully appear and a study of the accompanying specification and drawings, the invention consists of the novel constructions and combination of parts as will be more fully described hereafter but it is to be understood that changes and modifications may be resorted to without departing from the spirit and nature of the invention as claimed:

In the drawings:

FIG. 1 is a side view in cross section of both ends of an elongated medical catheter having a solid material supported near one end thereof and means for ejecting such solid material from the end of the catheter.

Figure 2:
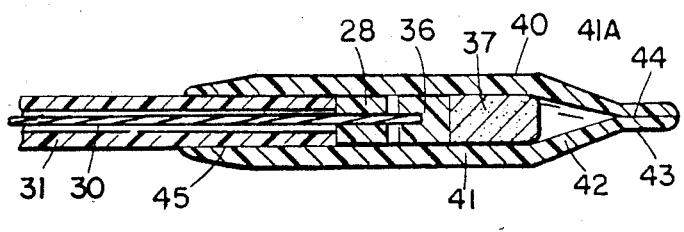
Figure 3:
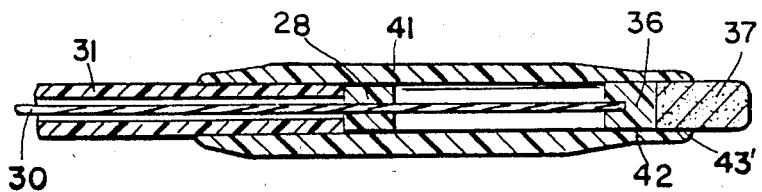

FIG. 2 is a side view in cross section of a modified form of the head end of the catheter of FIG. 1 wherein said head end contains a flexible wall portion which is normally closed and which may be opened by applying a force thereto through the material to be ejected from the other end of the catheter, and FIG. 3 is a side view in cross section of the device of FIG. 2 showing the solid material thereof being ejected from the end of the catheter.

In FIG. 1 is shown a first form of the invention comprising an assembly 10 formed of an elongated flexible hollow tube 31 made of a flexible plastic such as an elastomeric polymer or rubber and connected at one of its ends to an actuating device 11 which may be manually operated for urging the longitudinal movement of a flexible shaft 30 in the flexible tube 31, the combination defining what will be referred to hereafter as an ejection catheter. Depression of an actuator head or push button 20 by the movement of the human thumb thereagainst while a flange 12 forming part of the actuating device 11 is held by the fingers of the hand, urges shaft 30 longitudinally through the tube 31. The other end of tube 31 is inserted into a bore or opening 35 in a head or fitting 32 located at the end of the catheter, which fitting is an elongated bead-like hollow housing not much greater in diameter than the tube 31 and serving as a retainer and guide for a device or quantity of solid material to be implanted into the tissue adjacent said head when the latter is disposed at a given location in a body duct, such as an artery, the intestine, throat or other body duct. Fitting 32 has a tapered forward end 33 and a chamber defined by a cavity 34 of constant diameter extending from the end 33 thereof, into which chamber a piston 36 is slidably movable and is connected to the end of flexible shaft 30. Material, such as a medication in the form of a pill or solid cylinder 37, a viscous fluid such as a cream or salve, or a container for medication, is disposed within the chamber or cavity 34 in such a manner that it is normally retained therein but will be ejected from the end of the fitting when the piston 36 is urged forwardly by the forward movement of shaft 30. The material or pill 37 may be frictionally, adhesively or otherwise retained in chamber 34 so as to hold it therein until it is urged out of the operating end of head 32.

The actuating device 11 comprises a hollow tubular body 16 connected to the finger grip 13, through which body the flexible shaft 17 extends to the tubular retaining means 22 of the pushbutton head 20. When head 20 is pushed forwardly by the force applied by thumb thereagainst while fingers hold the grip 13, the push-pull shaft 30 is urged forwardly through the flexible tube 31 and the piston 36 which is connected to the end of said shaft, is thereby urged forwardly in the cavity or chamber 34 so as to force the device or medication 37 which is disposed against or forwardly of the piston, out of the end of the fitting 32 and preferably, although not necessarily, completely from the end of said fitting so as to dispose the device 37 adjacent to tissue which surrounds or is adjacent the head or fitting 32.

The end of flexible tube 31 is adhesively bonded or welded to the tapered rear end 35 of the head end or fitting 32 of the catheter and is shown abutting a cylindrical plug 28 containing a passageway 29 extending axially therethrough which serves as a lineal bearing in which the flexible shaft 30 may be longitudinally driven forwardly and rearwardly to urge the piston 36 to which it is connected, both forwardly and rearwardly. A helical spring 20S is shown disposed beneath the head 20 and a retaining wall portion 12 of the actuating assembly for normally urging the head 20 outwardly from the actuating end to maintain the piston 36 retracted prior to the ejection of the material 37 from the end of the head 32.

It is noted that a thin plastic film, wax or other material may be disposed across the opening in the cavity 34 of the head portion 32 of the catheter to maintain body fluids out of the passageway 34 until the wax or plastic film has been removed or ruptured by the forward movement of the solid material 37 as urged by piston 36 thereagainst. It is also noted that the finger operated actuating device 11 may be replaced by a pistol grip mechanism containing a trigger which is finger operated and is used to urge the flexible shaft 30 longitudinally in the bore of the flexible pipe or tube 31 for the purpose of ejecting the solid material or device 37 from the end of the head 32 or disposing at least a portion of 37 outwardly from the end of the head to engage or otherwise affect tissue within the human body adjacent the head.

In a second embodiment illustrated in FIGS. 2 and 3, the head end or fitting 40 of a catheter 39 has a tubular wall 41 having a tapered forward end 42, the end portion 43 of which is collapsed or formed closed, as illustrated, forming interface 44 which is normally in a sealing condition to close off the interior volume 41A until the tapered wall portion 42 is outwardly expanded so as to separate the interface 44 as illustrated in FIG. 3 when a piston 36 is urged forwardly by the forward movement of flexible shaft 30 it urges the solid cylindrical device or pill 37 through the tapered section 42 and the collapsed section 43 to either position it as illustrated in FIG. 3 protruding from the end of the end portion of the fitting 41 or to eject it completely therefrom so that it lies against the tissue adjacent the end of the catheter and may be utilized, by dissolving or other means, to beneficially effect such tissue, serve as a source of radiation if it is radioactive or other function depending on the physical and chemical characteristics of the material comprising the pill or plug 37. As provided in FIG. 1, the flexible pushpull shaft 30 is moved longitudinally in a flexible tube which is sealed within the rear portion of the bore of fitting 40 against the rear face of a thrust bearing or plug 28 and secured at its end to the piston 36 as described above. When the piston 36 is retracted to the position illustrated in FIG. 2, the memory of the plastic causes the outwardly expanded end 42 of the fitting 40 to collapse and assume the condition illustrated in FIG. 2 after which the catheter may be removed from the cavity or artery, sterilized and have a new device or plug of material 37 inserted therein for its next use.

What is claimed is:

1. A catheter or the like comprising in combination:
    an elongated flexible tube adapted to be inserted into and moved along a body duct such as an artery,
    an operating head attached to and terminating one end of said flexible tube,
    said operating head being formed of a flexible material and having a flexible front end portion which normally tapers from a first constant diameter portion to a smaller diameter at the front end of said head,
    said tapering portion of said head being tubular in configuration, a front end portion of said head being made of said flexible material and having opposite portions of the tubular wall thereof normally collapsed into abutment with each other so as to form a flattened tubular formation having a closed passageway therebetween at the front end of said tapering portion of said head, which closed passageway is an extension of the open tubular portion of said head and wherein the collapsed tubular wall thereof is expandable outwardly in a manner to open said passageway and form a tubular extension of the diameter portion of said head which extension is open at its end,
    the portion of said head located behind said normally collapsed portion of said head containing a quantity of material adapted to be dispensed from the end of said operating head,
    means extending through said head for urging movement of the material located within said head behind the collapsed portion thereby through said head and the flat closed passageway thereof at the end of said tapered portion of said head in a manner to expand the collapsed portion of said head so as to outwardly deform the opposite portions of the end of said head and to provide an open passageway therethrough to permit at least a portion of said material to pass completely through said head and to be expelled therefrom to the exterior of said head, and
    means at the other end of said elongated flexible tube for controlling the operation of said means for urging movement of said material through said head to permit said material to be dispensed beyond said head.

2. A catheter in accordance with claim 1 wherein said tapered front end portion of said head is constructed such that the opposite wall portions of said flexible tube self collapse against each other when such end portion of the flexible tube are void of material.

3. A catheter in accordance with claim 1 wherein said means for urging movement of said material through said tubular head comprises a piston which is slidably movable through said head and means controlled from the other end of said catheter for causing the sliding movement of said piston through said head to move material and to expand the collapsed portion of the flexible front end portion of said head and to cause said material to be expelled from the end of said head.

4. A catheter in accordance with claim 1 wherein said operating head is greater in diameter than said elongated tube.

5. A catheter in accordance with claim 3 including a tubular bearing supported within said operating head, a shaft supported for longitudinal movement within said bearing and connected to said piston and an extension of said shaft extending through said tube to the other end of said flexible tube and means connected to the other end of said shaft for urging longitudinal movement of said shaft in said tube and said bearing to cause longitudinal movement of said piston in said head, said piston being longitudinally movable through the end of said head.

* * * * *